United States Patent
Tsujii (10) Patent No.: US 9,259,158 B2
(45) Date of Patent: Feb. 16, 2016

(54) OBJECT INFORMATION ACQUIRING APPARATUS

(71) Applicant: CANON KABUSHIKI KAISHA, Tokyo (JP)

(72) Inventor: Osamu Tsujii, Kawasaki (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 91 days.

(21) Appl. No.: 13/719,609

(22) Filed: Dec. 19, 2012

(65) Prior Publication Data

US 2013/0197342 A1 Aug. 1, 2013

(30) Foreign Application Priority Data

Jan. 31, 2012 (JP) ................................. 2012-018305

(51) Int. Cl.
*A61B 5/05* (2006.01)
*A61B 5/00* (2006.01)
*G01N 21/17* (2006.01)

(52) U.S. Cl.
CPC .............. *A61B 5/0095* (2013.01); *A61B 5/0059* (2013.01); *G01N 21/1702* (2013.01); *A61B 5/7225* (2013.01)

(58) Field of Classification Search
CPC .. A61B 5/0095; A61B 5/7225; A61B 5/0059; G01N 21/1702
USPC ......................................................... 600/407
See application file for complete search history.

(56) References Cited

U.S. PATENT DOCUMENTS

| | | | |
|---|---|---|---|
| 4,589,783 A * | 5/1986 | Thomas et al. | 374/45 |
| 5,491,329 A * | 2/1996 | Urakami et al. | 250/205 |
| 7,564,998 B2 | 7/2009 | Tsujii | 382/128 |
| 2010/0070233 A1* | 3/2010 | Masumura | 702/127 |
| 2010/0087733 A1* | 4/2010 | Nakajima et al. | 600/437 |
| 2010/0191109 A1 | 7/2010 | Fukutani et al. | 600/437 |
| 2010/0331707 A1 | 12/2010 | Fukutani et al. | 600/476 |
| 2011/0083509 A1 | 4/2011 | Li et al. | 73/584 |

FOREIGN PATENT DOCUMENTS

| | | | | |
|---|---|---|---|---|
| JP | 2009-018153 A | 1/2009 | | A61B 8/00 |
| JP | 2010-088627 A | 4/2010 | | A61B 5/145 |
| WO | 2011/092069 A1 | 8/2011 | | |

OTHER PUBLICATIONS

Extended European Search Report issued Jun. 5, 2013 in counterpart EPA 13151163.6-1660.
Office Action issued on May 29, 2014 in counterpart Chinese (P.R.C.) patent application 201310031401.9, with translation.
Office Action issued on May 29, 2015, in counterpart Korean patent application 10-2013-0009032, with partial translation.

\* cited by examiner

*Primary Examiner* — Bo J Peng
(74) *Attorney, Agent, or Firm* — Fitzpatrick, Cella, Harper & Scinto (57) ABSTRACT

The present invention employs an object information acquiring apparatus including a plurality of light irradiators irradiating light from a light source to an object; an intensity modulator modulating intensity of the irradiated light for each light irradiator; a plurality of acoustic detectors detecting an acoustic wave generated from the object; and an information processor producing internal characteristic information of the object by using the acoustic wave, wherein the information processor controls a weight of each acoustic detector in production of the characteristic information, based on the intensity of light in each light irradiator.

6 Claims, 5 Drawing Sheets

OBJECT INFORMATION ACQUIRING APPARATUS

BACKGROUND OF THE INVENTION

1. Field of the Invention

The present invention relates to an object information acquiring apparatus.

2. Description of the Related Art

Studies on optical imaging techniques have been actively carried out which obtain in vivo information by irradiating light from a light source such as laser to a living body to propagate light in vivo and detect the propagated light and the like. One of the optical imaging techniques which has been proposed is photoacoustic tomography (PAT) (M. Xu and L. V. Wang "Photoacoustic imaging in biomedicine", Review of Scientific Instruments, 77, 041101 (2006)). Photoacoustic tomography is a technique in which pulsed light generated from a light source is irradiated to a living body, acoustic waves generated from body tissues which have absorbed light energy propagated and diffused in vivo are detected at a plurality of points and the signals thereof are analyzed and processed to visualize in vivo information. By this technique, the in vivo distribution of the value of optical characteristics, particularly the distribution of the optical energy absorbed density can be acquired. Such an in vivo imaging technique is also referred to as image reconstruction.

According to M. Xu and L. V. Wang "Photoacoustic imaging in biomedicine", Review of Scientific Instruments, 77, 041101 (2006), the acoustic pressure (P) of acoustic waves (photoacoustic waves) obtained from an absorber in vivo by light absorption in photoacoustic tomography can be represented by the following formula (1):

$$P = \Gamma \cdot \mu a \cdot \Phi \quad (1)$$

wherein $\Gamma$ is the Gruneisen coefficient which is a characteristic value of elasticity and is obtained by dividing the product of the volume expansion coefficient ($\beta$) and the square of the speed of sound (c) by the specific heat (Cp); $\mu a$ is the absorption coefficient of the absorber and $\Phi$ is the light quantity in a local area (the light quantity irradiated to the absorber).

It is known that the Gruneisen coefficient $\Gamma$ is almost constant when a tissue is identified. Accordingly, by performing at a plurality of points time-resolved measurement of change in the acoustic pressure P, which corresponds to the degree of an acoustic wave, the product of the absorption coefficient $\mu a$ and the light quantity $\Phi$, i.e., the distribution of the optical energy absorbed density can be obtained.

Japanese Patent Application Laid-open No. 2009-018153 discloses an example of an apparatus based on photoacoustic tomography. This apparatus utilizes relative positional information between an irradiated region and a light absorber in vivo and the acoustic pressure of acoustic waves when signals based on photoacoustic waves are analyzed to determine the distribution of the value of optical characteristics. Accordingly, it is sought to obtain the in vivo distribution of the value of optical characteristics with high resolution, particularly the distribution of the light absorption coefficient or the in vivo average equivalent attenuation coefficient and to accurately visualize them.

Japanese Patent Application Laid-open No. 2010-088627 discloses another example of an apparatus based on photoacoustic tomography. This apparatus utilizes the in vivo distribution of the light quantity determined based on the shape of a living body in order to obtain in vivo information from electric signals based on photoacoustic waves.

Patent Literature 1: Japanese Patent Application Laid-open No. 2009-018153
Patent Literature 2: Japanese Patent Application Laid-open No. 2010-088627
Non Patent Literature 1: M, Xu, L. V. Wang "Photoacoustic imaging in biomedicine", Review of scientific instruments, 77, 041101 (2006)

SUMMARY OF THE INVENTION

In photoacoustic tomography, it is preferable to decrease noise of calculation during operation process in order to obtain appropriate images by image reconstruction. Therefore, it is desirable to ensure uniform light quantity distribution in a target. By ensuring uniform light quantity distribution in vivo, an incident light quantity per unit time can be limited to a predetermined value or lower to reduce damage to the living body while the possibly strongest light within a predetermined range can be irradiated.

In order to ensure uniform light irradiation in vivo, it is preferable to irradiate light from a light source, from a plurality of directions at a plurality of irradiation sites. However, on the other hand, when any of these irradiation sites is positioned in the vicinity of an acoustic wave detector, the detected acoustic wave value may increasingly contain noise. This is caused by the noise in the electric circuit of the acoustic wave detector or the photoacoustic effect from components of the acoustic wave detector themselves. As a result of such a phenomenon, it is known that the result of reconstruction also contains noise and artifacts may be contained in images.

With the foregoing in view, an object of the present invention is to provide a technique which can reduce noise in photoacoustic tomography.

The present invention provides an object information acquiring apparatus comprising:

a plurality of light irradiators configured to irradiate light from a light source to an object;

an intensity modulator configured to modulate intensity of the irradiated light for each of the plurality of light irradiators;

a plurality of acoustic detectors configured to detect an acoustic wave generated from the object irradiated with the light; and an information processor configured to produce internal characteristic information of the object by using the acoustic wave, wherein the information processor controls a weight of each of the plurality of acoustic detectors in production of the characteristic information, based on the intensity of light in each of the plurality of light irradiators that has been modulated by the intensity modulator.

According to the present invention, the technique which can reduce noise in photoacoustic tomography can be provided.

Further features of the present invention will become apparent from the following description of exemplary embodiments with reference to the attached drawings.

DESCRIPTION OF THE EMBODIMENTS

Preferable embodiments of the present invention are described hereinbelow with referring to the figures. However, dimensions, materials and shapes of the components described hereinbelow and relative positions thereof and the like should be appropriately modified according to the configurations and various conditions to which the present invention is applied, and thus the following descriptions do not intend to limit the scope of the invention.

The biological information processing apparatus described herein is used for the purposes of diagnoses of malignant tumor or vascular diseases, follow-up assessments of chemotherapies and the like. The biological information processing apparatus acquires the in vivo distribution of the value of optical characteristics and characteristic information obtained therefrom such as the distribution of the concentration of a biological tissue constituting substance, the distribution of the initial acoustic pressure in an object, the distribution of the optical energy absorbed density derived from the distribution of the initial acoustic pressure, the distribution of the absorption coefficient and the like. The distribution of the concentration of a substance refers to, for example, the distribution of oxygen saturation, the distribution of the oxy- and deoxyhemoglobin concentration and the like. Based on the characteristic information, the apparatus can create an image of the inside of an object, i.e., can perform image reconstruction. Namely, the biological information processing apparatus of the present invention can be also referred to as an object information acquiring apparatus.

The acoustic wave as used herein refers typically to an ultrasound wave and includes elastic waves referred to as sound waves, ultrasound waves and acoustic waves. The acoustic wave generated by the photoacoustic effect is called as a photoacoustic wave or photo-ultrasound wave. The acoustic wave detector (e.g. a probe) receives the acoustic wave generated or reflected in the object.

First Embodiment

Figure 1:
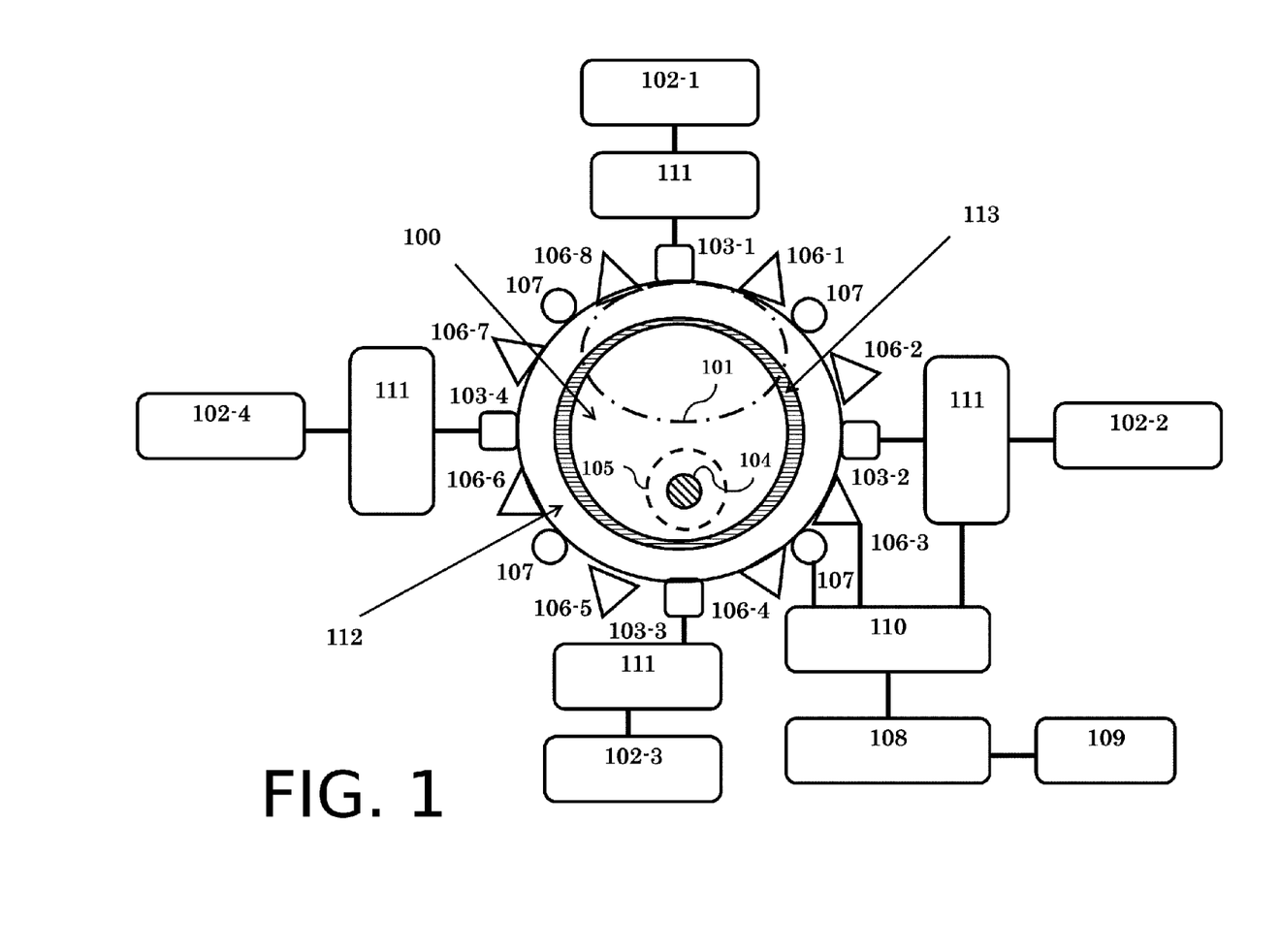
FIG. 1 is a plan view showing the configuration of a biological information processing apparatus according to the first embodiment.

FIG. 1 shows the configuration of the biological information processing apparatus according to the first embodiment of the present invention. The first embodiment of the present invention is described based on FIG. 1.

(Configuration of Apparatus)

The biological information processing apparatus comprises a light source 102, an optical coupler 103, an acoustic wave detector 106, a light quantity meter 107, a reconstructing unit 108, a display unit 109, a control unit 110, an intensity modulator 111 and a fixing member 112. In this embodiment, the object to be measured (target) is a living body 110.

The light source 102 emits light 101 and four light sources are shown in this FIGS. 102-1 to 102-4).

The light source generates light having the specific wavelength so as to be absorbed by the specific component among the components constituting the living body. The light source comprises at least one pulsed light source which can generate pulsed light on the order of a few nanoseconds to a few hundred nanoseconds. The light source is preferably a laser or alternatively, it may be a light emitting diode. Various lasers can be used such as solid-state laser, gas laser, dye laser, semiconductor laser and the like. Light to be used preferably has the wavelength in the near-infrared region of 700 nm or more and 1100 nm or less which is less absorbed in vivo. However, when the distribution of the value of optical characteristics of biological tissues rather close to the surface of the living body is sought to be determined, it is also possible to use the broader wavelength range, e.g., the wavelength range of 400 nm or more and 1600 nm or less. When the light source 102 is a semiconductor laser, intensity modulation can be conveniently carried out by current or voltage control.

The optical coupler 103 is an optical system formed with, for example, a lens, a mirror, an optical fiber and the like. The optical coupler 103 introduces light which has been emitted from the light source 102 and then modulated for intensity by the intensity modulator 111 into the living body 100 as light 101 via the fixing member 112. In this figure, four optical couplers (103-1 to 103-4) are shown in conformity with the number of the light sources. The optical coupler corresponds to a light irradiator of the present invention.

When partial energy of light propagated in the living body 100 is absorbed into a light absorber 104 such as a blood vessel, the light absorber 104 generates an acoustic wave 105. The acoustic wave detector 106 detects the acoustic wave 105 generated from the light absorber 104 and converts the acoustic wave signal into an electric signal. The acoustic wave detector corresponds to an acoustic detector of the present invention.

The fixing member 112 fixes the living body 100 in the biological information processing apparatus. The fixing member 112 is formed of a material which propagates light, particularly near-infrared light and a sound wave. Specific examples may include transparent resins and transparent glass. When there is a gap between the living body 100 and the fixing member 112, a filler 113 is provided. The filler 113 is a material which propagates light, particularly near-infrared light and a sound wave and may be matching liquid such as water. In order to ensure that there is no gap between the living body 100 and the fixing member 112, it is also possible to reduce the pressure of the living body 100 and the fixing member 112 with a decompression device (not shown) or to change the shape of the fixing member 112.

The light quantity meter 107 is a light detector for measuring the light quantity data from the living body 100. The light quantity meter 107 measures intensity of light which has been irradiated from the optical coupler, propagated in vivo and again reached to the surface of the living body after diffusion and absorption in body tissue. In the present embodiment, a plurality of light quantity meters 107 are provided (four in this figure) and a plurality of light quantity data are obtained as measurement results. In the control unit 110, the light quantity distribution in the living body 100 is estimated based on the light quantity data resulting from measurements. The light quantity distribution can be estimated by irradiating light simultaneously from a plurality of light sources 102 and measuring the light quantity at each light quantity meter. It can also be estimated by irradiating light from one of the plurality of light sources, estimating the light quantity distribution by this light source and repeating these steps a plurality of times.

The display unit 109 is a device displaying image information reconstructed by the reconstructing unit 108. In the biological information processing apparatus of the present invention, the display unit 109 is not an essential component. Another display device connected to the biological information processing apparatus may be used as the display unit 109.

The control unit 110 controls the acoustic wave detectors 106, the light quantity meters 107 and the intensity modulators 111. A plurality of ways of control by the control unit 110 may be contemplated. An information processor of the present invention corresponds to the reconstructing unit and the control unit, and can be realized by information processor and the like which comprises a processor and follows a program to act.

(Process Flow)

Figure 4:
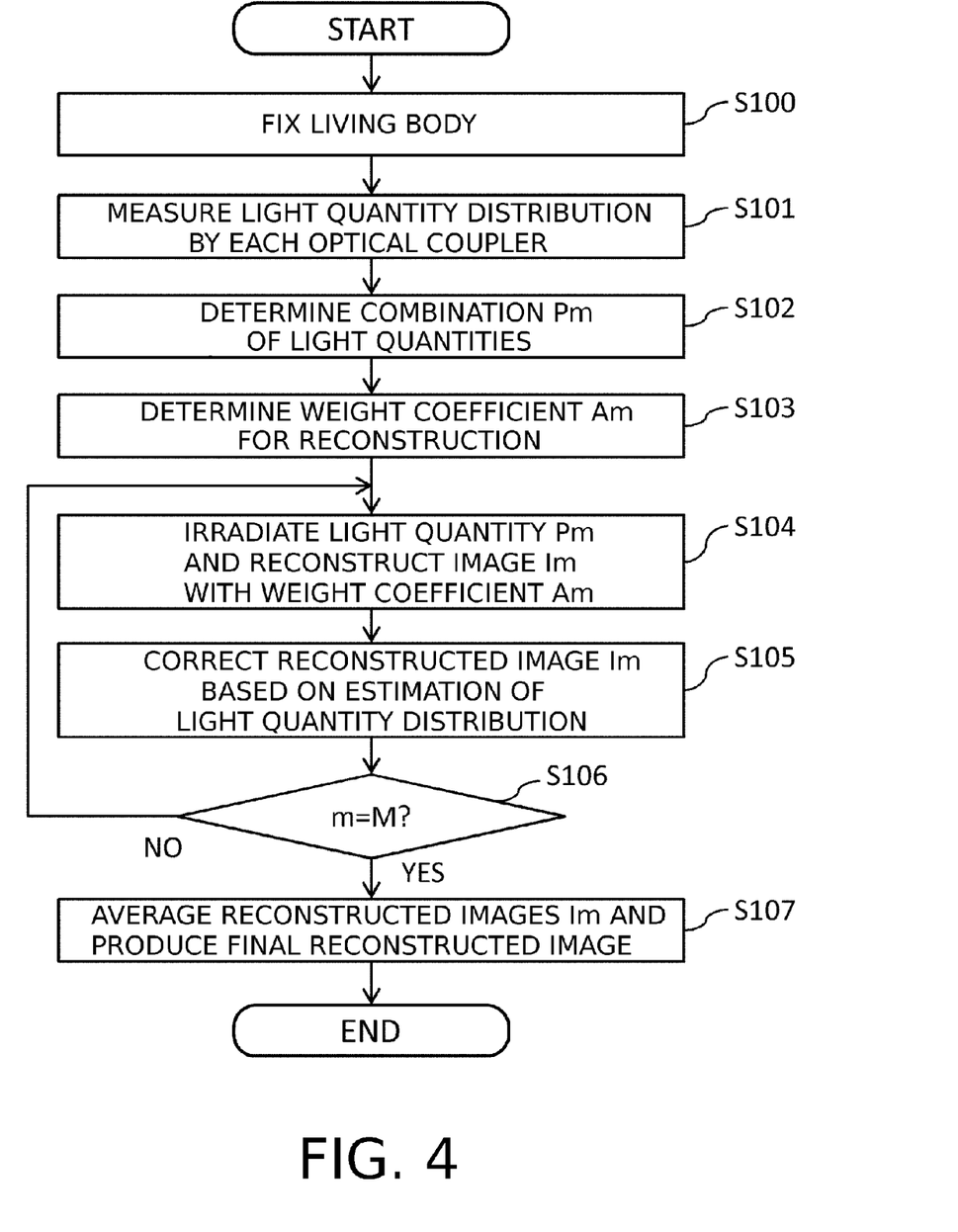
FIG. 4 is a flow chart of the process according to the first embodiment.

FIG. 4 shows a schematic flow chart of the present invention. In this figure, steps S100 to S103 are preparation procedures and in steps S104 to S107, actual photoacoustic measurement and in vivo imaging are carried out.

First, the living body 100 is fixed on the fixing member 112 (step S100).

Next, the light quantity distribution is measured for each optical coupler 103 (step S101). Specific procedure is described in detail hereinbelow. Briefly, in this procedure, an approximate light quantity of light irradiated from each optical coupler in pixels upon in vivo imaging is estimated.

Next, the combination Pm of irradiated light quantities is determined (step S102). Namely, an actual light quantity irradiated from each optical coupler to the living body is determined.

The reconstruction weight coefficient Am for each Pm is then determined (step S103).

Actual data collection is initiated thereafter. First, irradiation of light having the light quantity Pm, reception of acoustic waves propagated from the object and image reconstruction based on the acoustic waves are carried out (step S104). In this situation, the intensity modulator controls each optical coupler so as to irradiate light having the light quantity Pm. Upon reconstruction, the weight coefficient Am described above is applied. Accordingly, a reconstructed image Im is calculated.

The reconstructed image Im is then corrected according to the estimation of the light quantity distribution. Specifically, the light quantity distribution is corrected by dividing the reconstructed image Im by the estimated light quantity distribution (step S105).

While varying the light quantity Pm, the steps S104 and S105 are repeated for a predetermined times M (step S106).

Finally, the corrected reconstructed images Im are averaged to obtain a final reconstructed image (step S107).

(Weight Control)

The above respective procedures are now studied in detail.

In order to address the problem of the invention, inclusion of noise due to light irradiation in the vicinity of an acoustic wave detector, a simple manner may be taken in which the acoustic data obtained at the acoustic wave detector in the vicinity of the optical coupler irradiating light is not employed for image reconstruction. Alternatively, another manner may be taken in which the degree of contribution to a reconstructed image by the acoustic data from the acoustic detector in the vicinity of the optical coupler is decreased.

First, the way in which the acoustic data from the acoustic detector in the vicinity of the optical coupler is not used at all is described. In FIG. 1, when light is irradiated from the optical coupler 103-1, the acoustic data from the acoustic wave detectors 106-1 and 106-8, which may contain noise, are not used for image reconstruction (T=1 in Table 1). The thus obtained reconstructed image 1 has reduced noise.

On the other hand, when light is irradiated from the optical coupler 103-3, the acoustic data from the nearby acoustic wave detectors 106-4 and 106-5 are not used for image reconstruction (T=3 in Table 1). Similarly, in cases where light is irradiated from the optical couplers 103-2 and 103-4, the acoustic data from the nearby acoustic detector(s) are not used.

The above manner of control is summarized in Table 1.

TABLE 1

|  | Time | | | |
| --- | --- | --- | --- | --- |
|  | T = 1 | T = 2 | T = 3 | T = 4 |
| Irradiating optical coupler | 103-1 | 103-2 | 103-3 | 103-4 |
| Acoustic wave detector(s) used for reconstruction | 106-2 106-3 106-4 106-5 106-6 106-7 | 106-4 106-5 106-6 106-7 106-8 106-1 | 106-6 106-7 106-8 106-1 106-2 106-3 | 106-8 106-1 106-2 106-3 106-4 106-5 |
| Acoustic wave detector(s) not used for reconstruction | 106-1 106-8 | 106-2 106-3 | 106-4 106-5 | 106-6 106-7 |
| Reconstructed image | Reconstructed image 1 | Reconstructed image 2 | Reconstructed image 3 | Reconstructed image 4 |

The arithmetic mean of the reconstructed image 1 to reconstructed image 4 is calculated to produce the final reconstructed image. By calculating the arithmetic mean as above, a plurality of reconstructed images can compensate each other for the portions having low light quantity and low SN ratio of the images, thereby providing a preferable image.

Next, the way in which the degree of contribution to a reconstructed image by the acoustic data from the acoustic detector in the vicinity of the optical coupler is decreased is described. In this case, as shown in Table 2, the acoustic data obtained at each acoustic wave detector is weighted for respective reconstructed images. The weight means the weight coefficient used for arithmetic addition of reconstructed images.

In the example shown in Table 1, it can be construed that the weight for the acoustic wave detectors used for reconstruction is 1 and the weight for the acoustic wave detectors not used for reconstruction is 0. For example, in case of T=1, it can be construed that the weight for the acoustic wave detectors 106-1 and 106-8 is 0 and the weight for the acoustic wave detectors 106-2 to 106-7 is 1.

It is also possible to weight for example between 0 and 1.

Table 2 shows such a manner of weighting. One of the criteria for determination of the weight is a distance from the optical coupler irradiating light to each acoustic wave detector. Namely, the weight for the acoustic wave detector(s) having a short distance from the optical coupler is decreased because the detector(s) tends to contain noise (106-1 and 106-8 in case of T=1). Another criterion is a traveling distance of light from the optical coupler. Namely, a position(s) which has an increased distance from the optical coupler receives less amount of light, and therefore the weight for such a position(s) is decreased (106-4 and 106-5 in case of T=1). Accordingly, a plurality of reconstructed images compensate each other when the images are added.

TABLE 2

|  | Time | | | |
| --- | --- | --- | --- | --- |
|  | T = 1 | T = 2 | T = 3 | T = 4 |
| Irradiating optical coupler | 103-1 | 103-2 | 103-3 | 103-4 |

TABLE 2-continued

|  | Time | | | |
| --- | --- | --- | --- | --- |
|  | T = 1 | T = 2 | T = 3 | T = 4 |
| Weight coefficient for reconstruction of 106-1 | 0.01 | 0.25 | 0.09 | 0.15 |
| Weight coefficient for reconstruction of 106-2 | 0.25 | 0.01 | 0.15 | 0.09 |
| Weight coefficient for reconstruction of 106-3 | 0.15 | 0.01 | 0.25 | 0.09 |
| Weight coefficient for reconstruction of 106-4 | 0.09 | 0.25 | 0.01 | 0.15 |
| Weight coefficient for reconstruction of 106-5 | 0.09 | 0.15 | 0.01 | 0.25 |
| Weight coefficient for reconstruction of 106-6 | 0.15 | 0.09 | 0.25 | 0.01 |
| Weight coefficient for reconstruction of 106-7 | 0.25 | 0.09 | 0.15 | 0.01 |
| Weight coefficient for reconstruction of 106-8 | 0.01 | 0.15 | 0.09 | 0.25 |
| Reconstructed image | Reconstructed image 1 | Reconstructed image 2 | Reconstructed image 3 | Reconstructed image 4 |

The specific weight coefficient may be determined in consideration of only the distance from the optical coupler irradiating light to each acoustic wave detector. The weight coefficient may also be determined such that it is proportional to the distance from the optical coupler to each acoustic wave detector. Alternatively, it may also be determined by assuming that noise from the optical coupler irradiating light attenuates according to the square-root law or exponential law of the distance.

It is also possible to irradiate light from the plurality of optical couplers simultaneously. For example, in the manner shown in Table 3, light is irradiated from the opposing optical couplers. The weight coefficient is determined in consideration of the distance from the optical couplers irradiating light to each acoustic wave detector. In Table 3, the weight coefficient of the acoustic wave detectors which are close to the optical couplers irradiating light is 0. However, it may be a small value which is not zero. In this case, the data reaching to the acoustic wave detectors which are close to the optical couplers irradiating light can be reflected in reconstruction in some extent.

TABLE 3

|  | Time | |
| --- | --- | --- |
|  | T = 1 | T = 2 |
| Irradiating optical couplers | 103-1 103-3 | 103-2 103-4 |
| Weight coefficient for reconstruction of 106-1 | 0.00 | 0.25 |
| Weight coefficient for reconstruction of 106-2 | 0.25 | 0.00 |
| Weight coefficient for reconstruction of 106-3 | 0.25 | 0.00 |
| Weight coefficient for reconstruction of 106-4 | 0.00 | 0.25 |
| Weight coefficient for reconstruction of 106-5 | 0.00 | 0.25 |
| Weight coefficient for reconstruction of 106-6 | 0.25 | 0.00 |
| Weight coefficient for reconstruction of 106-7 | 0.25 | 0.00 |
| Weight coefficient for reconstruction of 106-8 | 0.00 | 0.25 |
| Reconstructed image | Reconstructed image 1 | Reconstructed image 2 |

(Estimation of In Vivo Light Quantity Distribution)

The further problem to be solved by the present invention, attainment of uniform light quantity in vivo, is now described. The estimation of the light quantity at this occasion precedes the actual photoacoustic measurement (S101); however, it is not always carried out. Alternatively to the estimation of the light quantity from the actual measured value, the light quantity may be determined based on the standard light propagation in vivo. The effect of reduction in noise of the present invention can be obtained by merely carrying out weighting as described above.

First, one of the plurality of optical couplers 103 is selected, light is irradiated therefrom and the in vivo light quantity distribution by the optical coupler is estimated. The estimation of the light quantity is repeated for the plurality of optical couplers.

Upon actual photoacoustic measurements, light can be irradiated from the plurality of optical couplers simultaneously, or from individual optical coupler. In the former case, by combining the light quantities estimated for respective optical couplers, the in vivo light quantity distribution when light is irradiated from the plurality of optical couplers simultaneously can be determined. The light quantity irradiated from each optical coupler can be controlled by the intensity modulator 111. Therefore, by controlling the intensity modulator based on the estimated value, the light quantity in vivo can also be corrected.

Light irradiated from the selected optical coupler propagates in vivo to reach to each light quantity meter. The irradiated light quantity is proportional to light reached to each light quantity meter. However, when the light quantity is too low, it cannot be detected due to the inherent noise of the light detector itself used as the light quantity meter. In this case, the intensity modulator alters intensity of light in order to irradiate light having at or higher intensity than the inherent noise of the light quantity meter. Attenuation of light depends on the properties of respective living bodies. Therefore, in order to ensure uniform light distribution in vivo, it is preferable to modulate intensity according to each living body. However, it is also possible to use a standard attenuation ratio or a value preliminarily measured with a living body of the same type.

A manner of control by the control unit 110 is now described in order to ensure uniform light quantity in vivo. The in vivo light quantity distribution can be determined by adding the in vivo light quantity distributions by light irradiated from respective optical couplers. In order to carryout this, light is irradiated from one of the optical couplers selected to a living body. A value is then measured at each light quantity meter 107. In this embodiment, the light quantity meters are provided at four different positions (107-1 to 107-4). Each light quantity meter is an one- or two-dimensional light detector and therefore each light quantity meter 107 measures light quantity at a plurality of points.

It is known that the light quantity propagated in vivo is attenuated exponentially in vivo as shown in the following formula (2):

$$\Phi = \Phi 0 \cdot \exp(-\mu \cdot d1) \quad (2)$$

wherein $\Phi 0$ is the incident light quantity, $\mu$ is the in vivo average attenuation coefficient from the light incident position to the light quantity meter and $d1$ is the distance from the light incident point to the light quantity meter.

The control unit estimates the in vivo light quantity distribution based on the measured values at respective light quantity meters. The light quantity distribution is estimated by backprojection to a three dimensional memory, interpolation and low-pass filtering. The three dimensional memory may be formed with a memory in the control unit (not shown).

Figure 2:
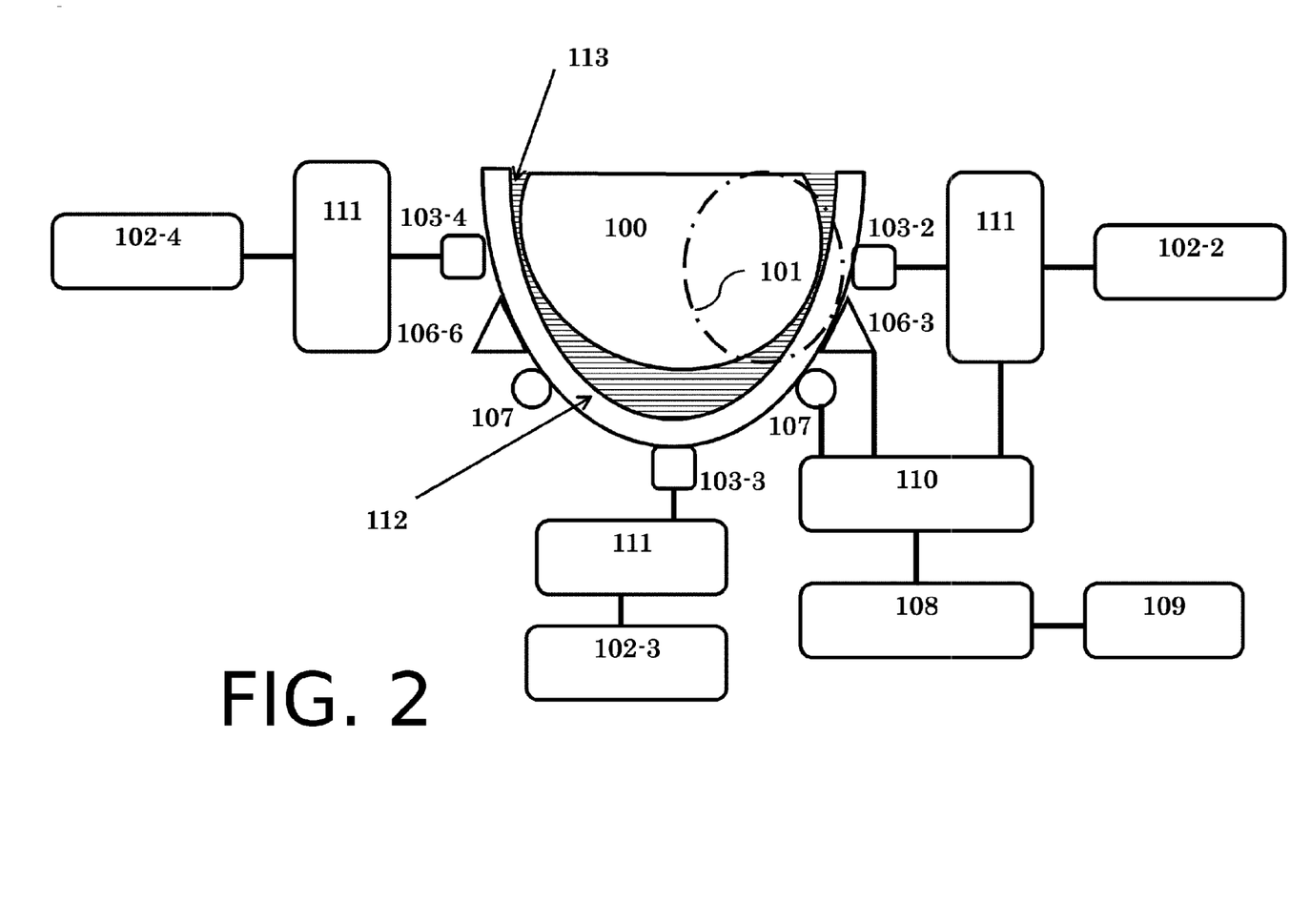
FIG. 2 is a side view showing the configuration of the biological information processing apparatus according to the first embodiment.

FIG. 2 is a side view of FIG. 1. The volume of the cube including the fixing member 112 corresponds to a cube 20 cm on a side. When the cube 20 cm on a side is resolved into pixels of 200×200×200, a pixel of three dimensional memory has 1 mm on a side. The position of the optical coupler irradiating light and the position of the light quantity meter are known on the three dimensional memory. The control unit then assigns to pixels on the line connecting the light quantity meter and the optical coupler the incident light quantity $\Phi 0$, the measured light quantity $\Phi$ and the light quantity calculated from the formula (2) (backprojection). The backprojection is performed for all light quantity meters 107. Accordingly, the light quantity of the pixels on this line is estimated.

In this embodiment, not all the outside surface of the fixing member is covered by the light quantity meters. Therefore, even after the backprojection for the pixels on the line, there are pixels remained for which the light quantity has not been estimated. The light quantity for such pixels can be determined by interpolation. In this embodiment, among various interpolation algorithms, linear interpolation is used.

Figure 3:
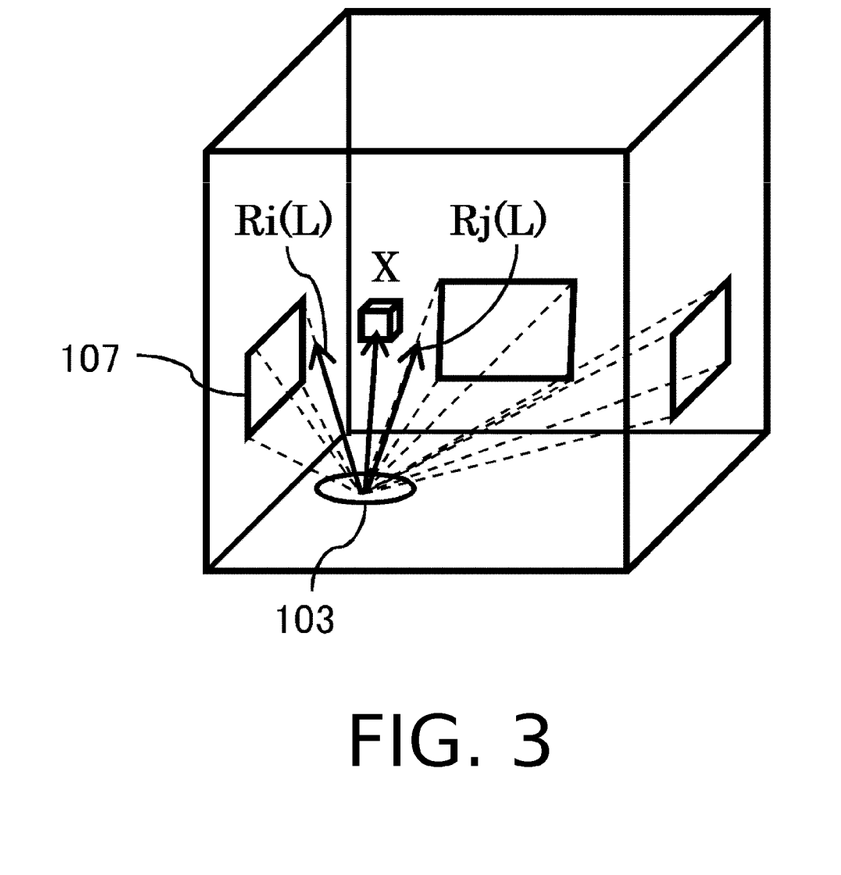
FIG. 3 is a conceptual view of reconstruction of the light quantity distribution according to the first embodiment.

The procedure for linear interpolation is described by referring to FIG. 3. On the surface of a cube simulating a living body, an optical coupler 103 and a light quantity meter 107 are provided. The light quantity of a pixel X near the center has not been estimated yet. The lines backprojected from the light quantity meter 107 to the optical coupler 103 are referred to as light beams Rn (n=1 . . . N and N is the number of light detectors included in the light quantity meter). It is assumed that the number of light beams when irradiated from an optical coupler 103 is the same as the number of light detectors constituting the light quantity meter 107.

The distance from the pixel X to the optical coupler 103 is designated as L. Two light beams Ri and Rj are chosen which have the shortest length Pn of the perpendicular line dropped from the pixel X to the light beam Rn. The light quantity of the light beams Ri and Rj at the distance L are referred to as Ri (L) and Rj (L). Then the light quantity XL of the pixel X can be represented by the formula (3):

$$XL=(Ri(L)+Rj(L))/2 \quad (3)$$

All pixels to which the light quantity has not been assigned are subjected to the calculation according to the formula (3). However, some pixels may require expedient determination of Rn (L) by extrapolation. When improvement in accuracy of light quantity estimation is desired, the formula may be appropriately modified according to the angle between the line from an optical coupler to a pixel and the line from the optical coupler to a light detector.

Then a three dimensional low-pass filter is performed on the three dimensional memory after interpolation. The formula (2) depicts the case in which light travels in a straight line while attenuating. However, light scatters in vivo and the scattered light also reaches to a light quantity meter. Light scattering can be regarded as a low-pass filter which decreases the contrast. Therefore, a three dimensional low-pass filter is performed on the three dimensional memory. An example of a usable low-pass filter is a relatively big kernel such as a 11×11×11 pixel. By performing a low-pass filter, estimation of the light quantity distribution for one optical coupler is completed. The same procedure is repeated for all optical couplers, the light quantities of respective pixels in respective optical couplers are added together, so that the light quantity distribution when light is irradiated simultaneously from a plurality of light sources can be determined.

The thus estimated light quantity can also be used for correction at the intensity modulator or correction upon image reconstruction.

(Correction of Light Quantity)

A manner for ensuring uniform light quantity distribution in vivo when light is irradiated simultaneously from the plurality of light sources is now described. An approximate solution is sufficient to ensure uniform light quantity distribution without necessity for determining a strict solution. This is because, as can be seen from the configurations in FIGS. 1 and 2, the light quantity at the central part of a living body is inevitably low and therefore it is difficult to ensure strict uniformity. Even when the light quantity distribution is uniform, it is necessary to take into account noise which an acoustic wave detector receives from an optical coupler. Various formulas may be contemplated as the evaluation function in order to evaluate uniformity of the in vivo light quantity distribution. In this embodiment, the evaluation function is employed which has the smallest difference between the light quantity at certain positions (more than one) in the three dimensional memory and the average light quantity.

When the light quantities of the optical couplers 103-1 to 103-4 are respectively designated as P1, P2, P3 and P4, the light quantity Bxyz at specific coordinates (X, Y, Z) in the three dimensional memory is represented by the formula (4):

$$Bxyz=Fxyz(P1,P2,P3,P4) \quad (4)$$

wherein Fxyz is a function which determines the light quantity at the coordinates (X, Y, Z) and is a linear function of P1, P2, P3 and P4. The coefficient of the linear function is determined by estimation of the light quantity distribution on each optical coupler 103.

By using the formula (4), the average light quantity Ba in a living body 100 is represented by the formula (5):

$$Ba=1/N \cdot \Sigma Fi(P1,P2,P3,P4) \quad (5)$$

wherein i=1 . . . N and N is coordinates within the living body 100.

The evaluation function H is represented by the formula (6):

$$H=\Sigma(Ba-Fj(P1,P2,P3,P4))^2 \quad (6)$$

wherein j=1 . . . K and represents specific coordinates within the living body 100. The specific coordinates are selected so as to be evenly distributed within the living body 100. K is determined so as to match the number of the optical couplers. In this embodiment, there are four optical couplers. Therefore, by defining K=4, P1, P2, P3 and P4 which minimize the evaluation function H can be determined.

The formula (7) is a simultaneous equation which minimize P1, P2, P3 and P4:

$$H/\partial Pj=0, (j=1 \ldots K) \quad (7)$$

For every combination of specific coordinates (four elements in this embodiment), P1, P2, P3 and P4 which satisfy the formula (7) can be determined.

A plurality of combinations of specific coordinates are selected. When respective combinations are designated as Sm (m=1 . . . M), the output intensity Pm=(Pm1, Pm2, Pm3, Pm4) from four optical couplers are determined for each Sm.

The light quantity (P1 to P4) is determined for each combination Sm and photoacoustic measurement is performed according to the determined light quantity. A reconstructed image Im is produced by one photoacoustic measurement and the Im (m=1 . . . M) are averaged to determine the final reconstructed image. Therefore, M is determined according to the SN ratio of each reconstructed image Im and a target SN ratio of the final reconstructed image. In this embodiment, M is 100. When M=100, the SN ratio can be obtained which is about ten times of each reconstructed image Im.

After determination of Pm (m=1 ... M), the weight coefficient Am of the acoustic wave detector is determined by taking into account of the amount of noise from the optical coupler. In this embodiment, eight acoustic wave detectors are used and therefore the weight coefficients of the acoustic wave detectors are represented as Am=(Am1...Am8). In this embodiment, Ami (i=1...8) is determined by assuming that the amount of noise of an acoustic wave detector due to the presence of an optical coupler decreases according to the square-root law of a distance. When the distance from the optical coupler 103-$i$ to the acoustic wave detector 106-$j$ is designated as Lij, Aj is represented by the formula (8):

$$Aj = C \cdot \Sigma Pi \cdot (Lij^2) \qquad (8)$$

wherein J=1...8. C is a coefficient and is determined so as to be ΣAj=1. After determination of Pm and Am, Pm (m=1... M) is driven in a time-series manner and the reconstructed image Im according to the determined Am is produced.

(Time Chart of Processing)

Figure 5:
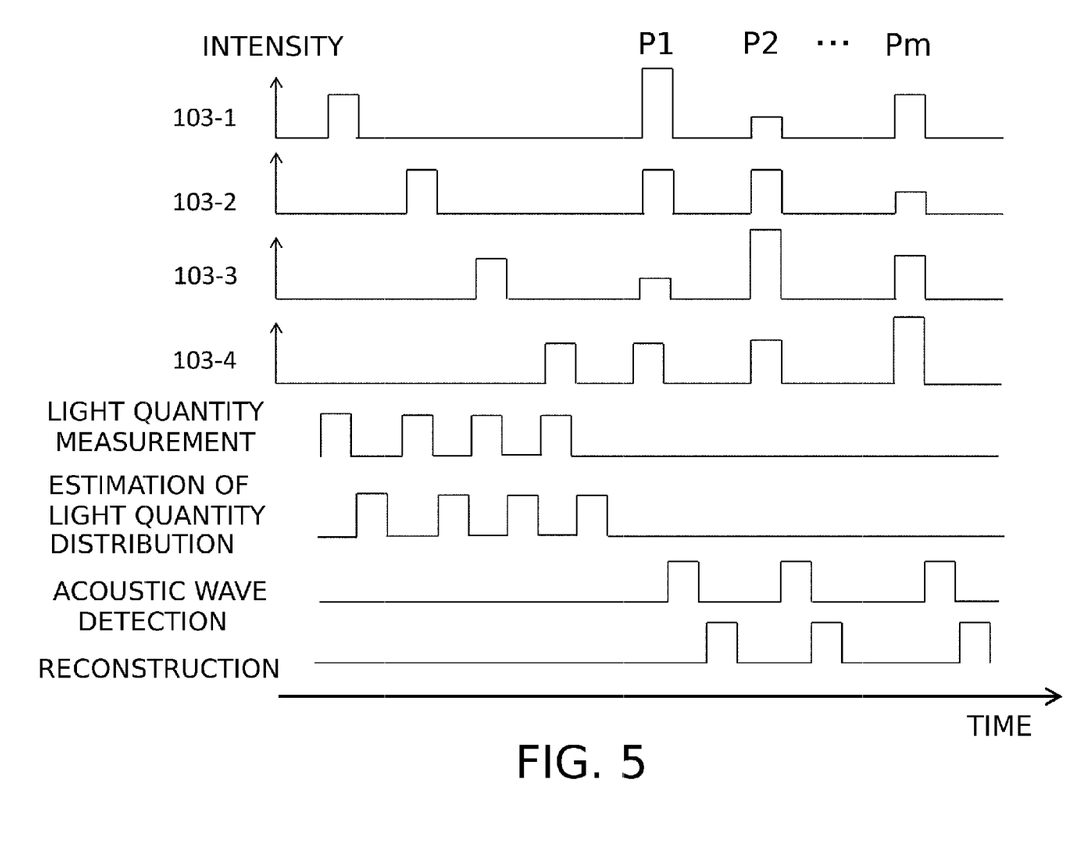
FIG. 5 is a time chart of modulation in light quantity intensity according to the first embodiment.

FIG. 5 shows a time chart in which light is irradiated with the light quantity distribution S101 and various light quantities Pm to reconstruct a reconstructed image Im.

The left side of this time chart corresponds to preparation stages prior to actual photoacoustic measurement and corresponds to S101 to S103 of the flow chart described above. The respective optical couplers 103-1 to 103-4 irradiate light having determined intensities and measurement at the light quantity meter and estimation of the light quantity distribution at the control unit are carried out. After the measurement of each optical coupler, the combination Pm of the light quantities and the weight coefficient Am are determined.

The right side of the time chart corresponds to actual photoacoustic measurement and corresponds to S104 and thereafter of the flow chart. Each optical coupler is controlled according to the light quantity Pm and M times of light irradiations, detection of acoustic waves accompanying to the irradiations and image reconstruction based on the acoustic waves are performed. All reconstructed images from respective cycles are averaged to produce the final reconstructed image.

Second Embodiment

When the light source is a laser light source, it is necessary to understand the light quantity or output irradiated in order to secure the safety of a living body. The second embodiment of the present invention, a method for decreasing damage by light on a living body, is described.

The biological information processing apparatus of the first embodiment described above allows estimation of the in vivo light quantity distribution based on the measured light quantity. This value corresponds to light output, i.e., to the amount of energy applied to a living body. Therefore, the estimation of the light quantity distribution allows calculation of the damage by light on a living body.

The control by the control unit based on estimation of the light quantity distribution predicted from the light quantity Pm allows limiting the incident light quantity per unit time to a predetermined value or lower. The predetermined value includes, for example, a value complying with safety standards. By averaging the light quantities, the amount of light can be increased as much as possible while complying with safety standards, thereby allowing production of much better reconstructed images.

As described above, the present invention allows controlling a plurality of light sources and a plurality of acoustic wave detectors to optimize the weights for reconstruction of each light quantity and each acoustic wave detector. It can also ensure approximately uniform light quantity distribution in an object. As a result, noise in a reconstructed image can be reduced.

In addition, by appropriately controlling the light quantity, damage to a target can also be decreased.

Therefore, the present invention can be suitably used for the technologies employing the photoacoustic effect, particularly in the field of in vivo information imaging of human and animals.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2012-018305, filed on Jan. 31, 2012, which is hereby incorporated by reference herein its entirety.

What is claimed is:

1. An object information acquiring apparatus comprising:
   a plurality of light irradiators configured to irradiate an object with light from a light source;
   an intensity modulator configured to modulate intensity of the irradiated light for each of the plurality of light irradiators;
   a plurality of acoustic detectors configured to detect an acoustic wave generated from the object irradiated with the light; and
   an information processor configured to produce internal characteristic information of the object by using the acoustic wave,
   wherein the intensity modulator changes a combination of the intensity of the light irradiated from the plurality of light irradiators, and
   wherein the information processor
   (a) changes a combination of weights of outputs of each of the plurality of acoustic detectors, for each of the combinations of the intensity of light in each of the plurality of light irradiators that has been modulated by the intensity modulator,
   (b) generates a plurality of images including one respective image for each of the combinations of weights, and
   (c) generates a final image by combining the plurality of images generated for each of the combinations of weights.

2. The object information acquiring apparatus according to claim 1, wherein the information processor controls respective weights for the plurality of acoustic detectors in production of the characteristic information, based on a light quantity distribution in the object.

3. The object information acquiring apparatus according to claim 2, further comprising a light quantity meter configured to measure intensity of the light irradiated from the light irradiators and propagated in the object,
   wherein the light quantity distribution in the object is estimated from a measurement result obtained by the light quantity meter.

4. The object information acquiring apparatus according to claim 2, wherein the intensity modulator reduces variation in light quantity in the object by modulating the intensity of light for each of the plurality of light irradiators based on the light quantity distribution in the object.

5. The object information acquiring apparatus according to claim 2, wherein the intensity modulator modulates the intensity of light for each of the plurality of light irradiators based on the light quantity distribution in the object to limit a light quantity irradiated to the object per unit time to a predetermined value or lower.

6. The object information acquiring apparatus according to claim 1, wherein, in production of the characteristic information, the information processor decreases a weight on an acoustic wave detected by an acoustic detector which is close to the light irradiator that has irradiated light, among the acoustic waves detected by the plurality of acoustic detectors.

* * * * *